United States Patent [19]

Flemer, III

[11] Plant 4,540

[45] May 27, 1980

[54] *PRUNUS SUBHIRTELLA*

[75] Inventor: William Flemer, III, Princeton, N.J.

[73] Assignee: Treesearch, Kingston, N.J.

[21] Appl. No.: 6,509

[22] Filed: Jan. 25, 1979

[51] Int. Cl.[2] ..... A01H 5/03

[52] U.S. Cl. ..... Plt./37

[58] Field of Search ..... Plt./37

*Primary Examiner*—Robert E. Bagwill

*Attorney, Agent, or Firm*—Frank B. Robb

[57] ABSTRACT

There is disclosed a flowering Higan Cherry Tree of the variety *Prunus subhirtella* which produces abundant quantities of deep purplish red blooms of semi-double form and long lasting qualities, the buds being capable of resisting bitter cold as low as minus 17 degrees F. in the vicinity of Princeton, N.J. under cultivated conditions.

2 Drawing Figures

The present invention relates to a new and distinct variety of flowering cherry tree of the species botanically known as *Prunus subhirtella,* which was discovered by me in a cultivated row of seedlings of the *Prunus subhirtella* variety known as "Autumnalis" (unpatented).

The variety is designated by me as "Pink Cloud", and when originally discovered by me was growing in a row of seedlings in my nursery which I operate and control and which is located in South Brunswick Township, N.J.

The seedling first attracted my attention because of the deep purplish pink color of the blooms which began flowering in early April, and as continued observations took place it was noted that the tree produced abundant, deep purplish pink semi-double flowers for a substantially long period of time, as a matter of fact very much longer than other Higan cherry trees growing in adjacent rows.

The close observation which was exerted, noted the semi-double nature of the blooms and the fact that they were very much more deep purplish pink than those of other cherry trees as before noted in the same general area.

The seedling which was selected and is here described, has been kept under close observation and in due course I caused the same to be asexually propagated by dormant grafting which has preserved the qualities of the parent tree, and has been carried on in my nursery above mentioned.

The continued observation of the seedling and progeny derived therefrom, confirmed that the form of the tree and the color of the blooms are established features thereof and along with other distinctive features noted during my observations and tests extending over a long period of time.

I am thereby convinced that my new seedling represents a new and improved variety of flowering cherry tree as particularly evidenced by the following unique combination of principal characteristics which are outstanding therein and which distinguish it from the "Autumnalis" variety, as well as from other varieties of flowering cherry trees of which I am aware:

1. Deep purplish pink color of the flowers;
2. Very abundant quantity of blooms produced;
3. The semi-double form of the flowers;
4. The ability of the flower buds to survive extremely low temperatures;

5. The long lastingness of the blooms averaging six days longer than other Higan cherry trees growing in adjacent rows.

Asexual reproduction of my new variety "Pink Cloud" by dormant grafting, as performed by me in my nursery located in South Brunswick Township, N.J., shows that the foregoing characteristics and distinctions come true and are established and transmitted through succeeding propagations.

The accompanying drawing which shows in the upper view the dense purplish pink nature of the blooms, is illustrative of the tree and indicates the habit of growth as well as typical flowers.

The lower view showing in the foregound a typical tree and the dense growth thereof with the color permeating the entire tree is also typical.

There follows a detailed description of my new variety of *Prunus subhirtella,* which is related to the disclosure above and the colors therein described in accordance with color terminology in comparison with the Nickerson Color Fan, published by Munsell Color Company, Inc., of Baltimore, Md., and are as nearly true as is possible to make the same in a color illustration of this kind and making allowance for variation in observation qualities of myself as compared with others.

Parentage: Seedling.

*Seed parent.*—*Prunus subhirtella* "Autumnalis".

*Pollen parent.*—Unknown.

Propagation: Holds its distinguishing characteristics through succeeding propagations by dormant grafting.

Locality where grown and observed: South Brunswick Township, N.J.

Tree: Small; spreading; dense; hardy.

*Trunk.*—Stocky; rough.

*Branches.*—Slender; rough. Color — strong yellowish brown 7.5 YR 5/7. Lenticels —dark, moderately abundant.

Foliage:

*Leaves.*—Quantity — abundant. Size — length — 8 to 9 cm. Width — 3 to 3.5 cm. Shape — lanceolate. Color — upper surface — moderate olive green 7.5 GY 4/4. Under surface — moderate yellow green 7.5 GT 5/7. Margin — serrate. Petiole — short — about 1 cm. in length. Glands — average number — 2. Opposite. Globose. Color — moderate reddish brown 7.5 R 3/6.

Flower buds:

*Hardiness.*—Very hardy; have withstood and survived −17° F. at Princeton, N.J. when the buds of other Japanese Cherry trees were killed.

*Size.*—0.2 cm. long.

*Shape.*—Ovate; pointed.

*Color.*—Chestnut brown.

Flowers:

*Borne.*—In clusters of 4 to 7 flowers.

*Bloom dates.*—First bloom — about April 1 in normal years. Full bloom — about April 10 in normal years.

*Quantity.*—Abundant; semi-double.

*Size.*—Medium; 2½ cm. in diameter.

Petalage:

*Number of petals.*—22 to 25.

*Shape of petals.*—Narrow oval with notched points.

*Size of petals.*— Length — about 1.2 cm. Width — about 0.6 cm.

*Color.*—In bud — strong purplish red 10 RP 4/12. Fully open — deep purplish red 7.5 RP 6/12.

Fruits: Not significant.

I claim:

1. A new and distinct variety of flowering cherry tree of the species botanically known as *Prunus subhirtella,* substantially as herein shown and described, characterized particularly as to novelty by the unique combination of the deep purplish pink color of the flower, the very abundant quantity of blooms, the semi-double form of the flowers, the ability of the flower buds to survive extremely low temperatures, and the long lastingness of the blooms averaging six days longer than other Higan Cherry Trees growing in the vicinity.

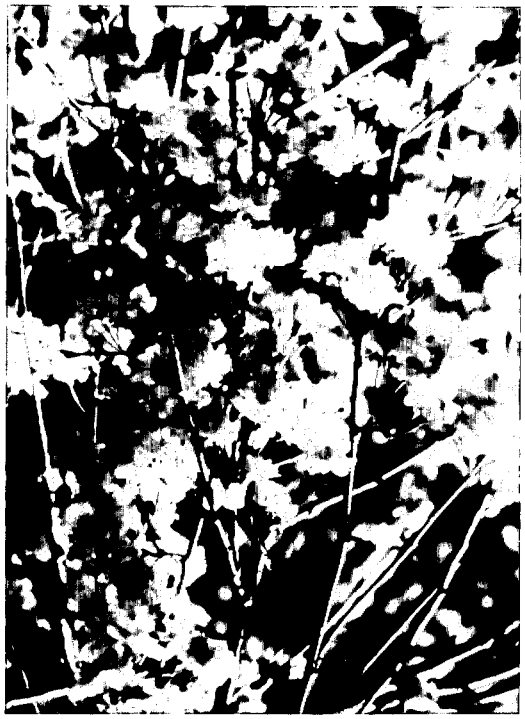
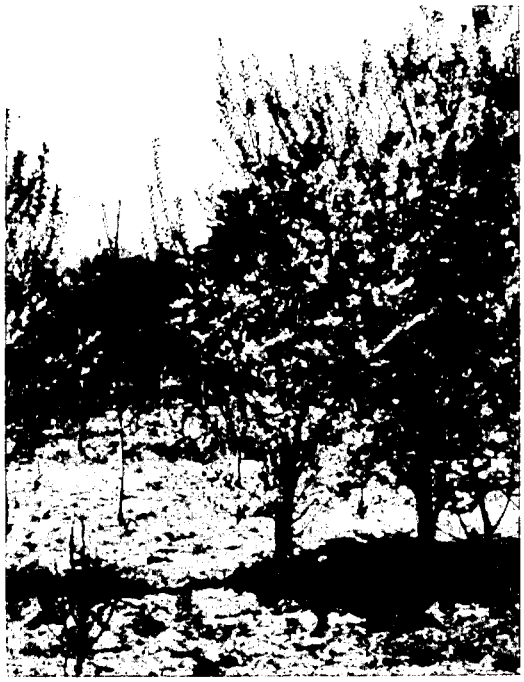

* * * * *